United States Patent
Warnick (10) Patent No.: US 8,043,293 B2
(45) Date of Patent: Oct. 25, 2011

(54) PIVOTABLE INTERBODY SPACER

(75) Inventor: David R. Warnick, Spanish Fork, UT (US)

(73) Assignee: Beacon Biomedical, LLC, Tequesta, FL (US)

( * ) Notice: Subject to any disclaimer, the term of this patent is extended or adjusted under 35 U.S.C. 154(b) by 606 days.

(21) Appl. No.: 11/726,865

(22) Filed: Mar. 22, 2007

(65) Prior Publication Data

US 2007/0225808 A1    Sep. 27, 2007

Related U.S. Application Data

(60) Provisional application No. 60/784,546, filed on Mar. 22, 2006.

(51) Int. Cl.
*A61B 17/70* (2006.01)

(52) U.S. Cl. ....... 606/86 A; 606/99; 606/249; 623/17.11

(58) Field of Classification Search ................ 606/86 A, 606/246–249, 95, 96, 99, 104; 623/17.11–17.16
See application file for complete search history.

(56) References Cited

U.S. PATENT DOCUMENTS

| | | | |
|---|---|---|---|
| 5,989,289 A | 11/1999 | Coates et al. | |
| 6,599,294 B2 | 7/2003 | Fuss et al. | |
| 6,696,073 B2 | 2/2004 | Boyce et al. | |
| 6,719,794 B2 | 4/2004 | Gerber et al. | |
| 6,830,570 B1 | 12/2004 | Frey et al. | |
| 6,942,697 B2 | 9/2005 | Lange et al. | |
| 6,974,480 B2 | 12/2005 | Messerli et al. | |
| 7,018,413 B2 | 3/2006 | Kruger | |
| 7,041,137 B2 | 5/2006 | Fulton et al. | |
| 7,060,073 B2 | 6/2006 | Frey et al. | |
| 2003/0139813 A1 | 7/2003 | Messerli et al. | |
| 2004/0097929 A1 | 5/2004 | Branch et al. | |
| 2004/0199251 A1 | 10/2004 | McCombe et al. | |
| 2005/0131536 A1* | 6/2005 | Eisermann et al. | 623/17.11 |
| 2007/0162128 A1 | 7/2007 | DeRidder et al. | |
| 2007/0213737 A1* | 9/2007 | Schermerhorn et al. | 606/86 |
| 2008/0009880 A1 | 1/2008 | Warnick et al. | |
| 2008/0140085 A1 | 6/2008 | Gately et al. | |
| 2008/0306488 A1 | 12/2008 | Altarac et al. | |

* cited by examiner

*Primary Examiner* — Eduardo C Robert
*Assistant Examiner* — Christina Negrelli
(74) *Attorney, Agent, or Firm* — McHale & Slavin, P.A.

(57) ABSTRACT

According to another exemplary embodiment, a pivotable interbody implant system includes an implant including a body defining an inner cavity and a plurality of teeth formed on one end of the implant, and an insertion instrument associated with the implant, wherein the insertion instrument includes a retractable latching mechanism and an internal gear configured to pivotably mate with said teeth formed on said implant.

12 Claims, 9 Drawing Sheets

PIVOTABLE INTERBODY SPACER

RELATED APPLICATIONS

This application claims the benefit under 35 U.S.C. §119 (e) of U.S. Provisional Patent Application No. 60/784,546 filed Mar. 22, 2006 titled "Pivotable Interbody Spacer," which provisional application is incorporated herein by reference in its entirety.

FIELD

The present system and method relate to bone fixation devices. More particularly, the present system relates to a spinal implant for interbody fusion to the spinal column.

BACKGROUND

A The degeneration of the intervertebral disk, in particular of the nucleus pulposus, results in a loss of height in the affected disk space which is associated with a weakening of the annulus fibrosus and of the ligaments. The spinal column hereby becomes instable at this position. The consequence is a horizontal displaceability of the vertebral bodies with respect to one another which results in impairments of the nerve roots in this region and/or of the spinal marrow with pain resulting therefrom.

The principle for the treatment of these symptoms consists of the surgical removal of the nucleus pulposus and the insertion of support bodies in order to restore the normal height of the disk space.

There are a variety of demands on both the surgeon performing an intervertebral disk procedure and on the spinal implants themselves.

A Transforaminal Lumbar Interbody Fusion (TLIF) is a posterior and lateral approach to the disc space. To gain access to the disc space, typically the facet joint is removed and access is gained via the nerve foramen. While more technically demanding of the surgeon than other fusion techniques, a TLIF offers a number of clinical advantages.

When compared to a PosteroLateral Fusion (PLF), a TLIF approach leaves much more of the soft tissue intact, which is less traumatic for the patient. Further, a PLF does not provide access to the disc space.

While a PosteroLateral InterBody Fusion (PLIF) provides access to the disc space, a TLIF approach also provides access to the interbody space, but without the need for manipulation of neural elements, reducing the risk of post-operative neural deficit. Additionally, in a TLIF, only a single implant is placed. More specifically the TLIF implant is placed in the anterior aspect of the disc space, thus providing space for a substantial fusion mass in the posterior aspect of the disc space where the natural compression occurs.

However, traditional TLIF procedures do suffer from shortcomings. For example, to place the desired implant in the anterior aspect of the disc space from an oblique posterior approach, traditional procedures demand that the implant be released from the inserter and then tamped into place. The two step insertion of this implant is generally recognized among surgeons as cumbersome.

SUMMARY

According to one exemplary embodiment, a pivotable interbody implant includes a body defining an inner cavity and a plurality of teeth formed on one end of said implant.

According to another exemplary embodiment, a pivotable interbody implant system includes an implant including a body defining an inner cavity and a plurality of teeth formed on one end of the implant, and an insertion instrument associated with the implant, wherein the insertion instrument includes a retractable latching mechanism and an internal gear configured to pivotably mate with said teeth formed on said implant.

Furthermore, according to one exemplary embodiment, a method for pivotably implanting an interbody implant includes coupling the implant to a pivoting instrument, inserting the implant through a nerve foramen, pivoting the implant from one end to allow further insertion until the implant is inserted to its final position, and releasing the implant from the instrument and removing the instrument.

BRIEF DESCRIPTION OF THE DRAWINGS

The accompanying drawings illustrate various exemplary embodiments of the present system and method and are a part of the specification. Together with the following description, the drawings demonstrate and explain the principles of the present system and method. The illustrated embodiments are examples of the present system and method and do not limit the scope thereof.

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Throughout the drawings, identical reference numbers designate similar but not necessarily identical elements.

DETAILED DESCRIPTION

The present specification describes a system and a method for pivotably inserting an interbody spacer, such as during a Transforaminal Lumbar Interbody Fusion (TLIF). According to one exemplary embodiment, a system including a pivotable interbody implant and insertion instrument configured to pivotably manipulate the pivotable interbody spacer are provided herein. According to one exemplary embodiment, a plurality of teeth are formed on at least one end of the implant and an insertion instrument associated with the implant. According to one exemplary embodiment, the insertion instrument includes a retractable latching mechanism for coupling an end of the pivotable interbody implant and an internal gear configured to pivotably mate with the teeth formed on at least one end of the implant. Further details of the present exemplary system and method will be provided below, with reference to the figures.

In the following description, certain specific details are set forth in order to provide a thorough understanding of various embodiments of the present system and a method for pivotably inserting an interbody spacer. However, one skilled in the relevant art will recognize that the present exemplary system and method may be practiced without one or more of these specific details, or with other methods, components, materials, etc. In other instances, well-known structures associated with interbody fusion have not been shown or described in detail to avoid unnecessarily obscuring descriptions of the present exemplary embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment. Furthermore, the particular features, structures, or characteristics may be combined in any suitable manner in one or more embodiments.

Exemplary Structure

Figure 1A:
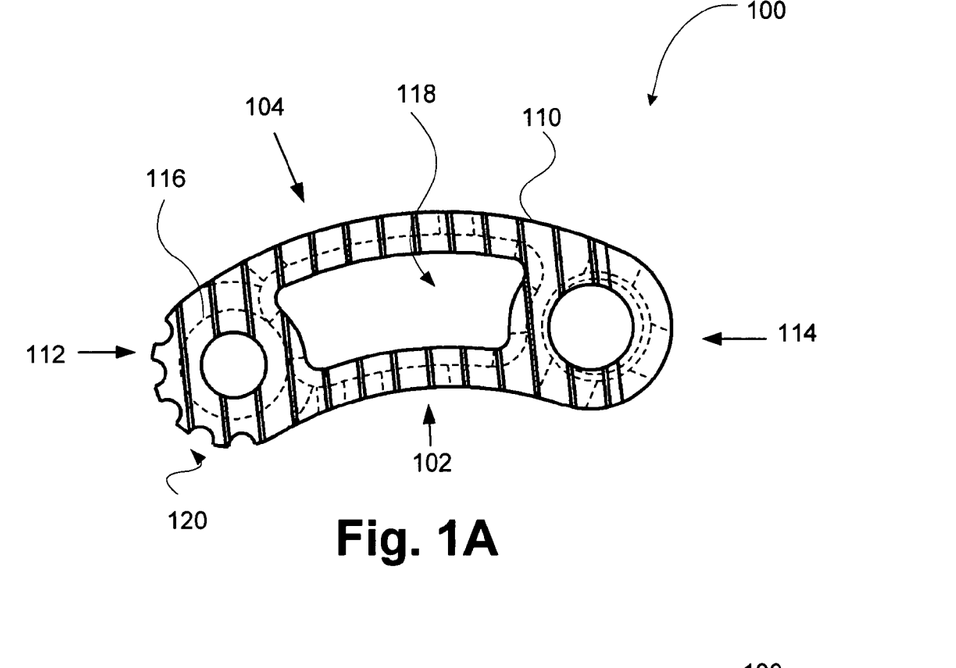
FIGS. 1A and 1B are a side view and a perspective view, respectively, of a pivotable interbody implant, according to one exemplary embodiment.
Figure 1B:
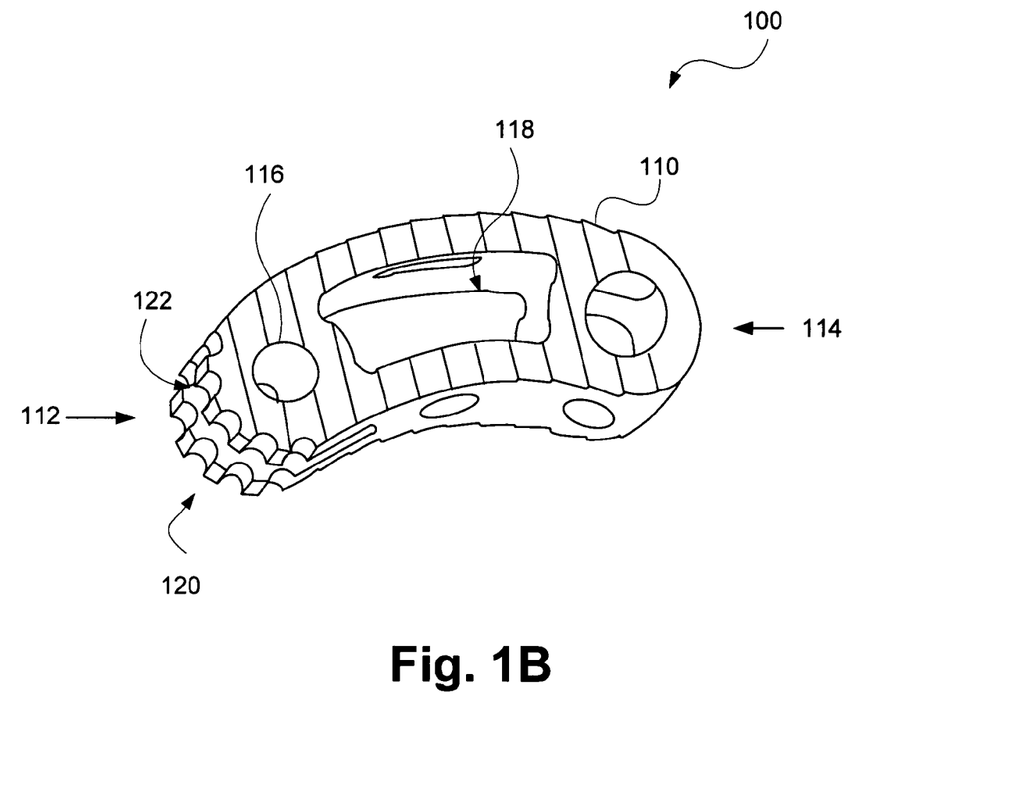

FIGS. 1A and 1B illustrate an interbody implant (100), according to one exemplary embodiment. As illustrated in FIGS. 1A and 1B, the present exemplary interbody implant (100) is designed for use as an intervertebral spacer in spinal fusion surgery, where an affected disk is removed from between two adjacent vertebrae and replaced with an implant that provides segmental stability and allows for bone to grow between the two vertebrae to bridge the gap created by disk removal.

As shown, the present exemplary interbody implant (100) has an arcuate, "rocker-like" body (100) with curved anterior and posterior faces (102, 104), respectively to facilitate the offset insertion of the implant through a narrow approach window into the disk space. As illustrated, the present interbody implant (100) includes a proximal end (112) that will be closest to a surgeon during use, and a distal end (114) that will likely be the leading edge of insertion during use.

The internal portion of the implant body (110) defines a hollow center. With the advent of bone morphogenic protein (BMP), the implant is now seen as a potential delivery tool of the BMP. consequently, many implants are now hollow. However, the size of the internal cavity of the implant is limited by the need to limit the size of the implant and to maximize the surface area of the implant. Too large of an implant will not provide space for a fusion mass. Too small of a surface area will lead to subsidence of the implant into the adjacent vertebral bodies. Consequently, the present exemplary interbody implant (100) employs geometry that provides for a small implant with relatively large surface area and internal cavity. According to one embodiment, the implant is hollowed out to increase cavity volume and surface area while minimizing overall size.

Additionally, as illustrated in FIGS. 1A and 1B, the present interbody implant (100) includes a plurality of teeth (120) or other frictionally engaging features on at least one end of the implant (100). According to one exemplary embodiment, any number of protruding features, materials, or rough surface finishes performed on at least one end of an interbody implant (100) may be used to pivotably direct an interbody implant during use. Particularly, according to one exemplary embodiment, the present exemplary interbody implant (100) Additionally the teeth (120) provide for rotation of the TLIF implant for final positioning without having to release it and tamp it in place.

As shown, particularly in FIG. 1B, the teeth (120) or other frictionally engaging features are formed on the perimeter of at least one end of the implant. As shown, the teeth define an access gap (122) that allows access to internal features of the interbody implant (100), such as the internal transverse cylinder (116) illustrated in FIGS. 1A and 1B. Alternatively, the teeth (120) or other frictionally engaging features may be formed inside the access gap (122). For ease of explanation only, the present specification will describe the present system and method in the context of an implant including external teeth (120) on at least one end thereof.

Figure 2:
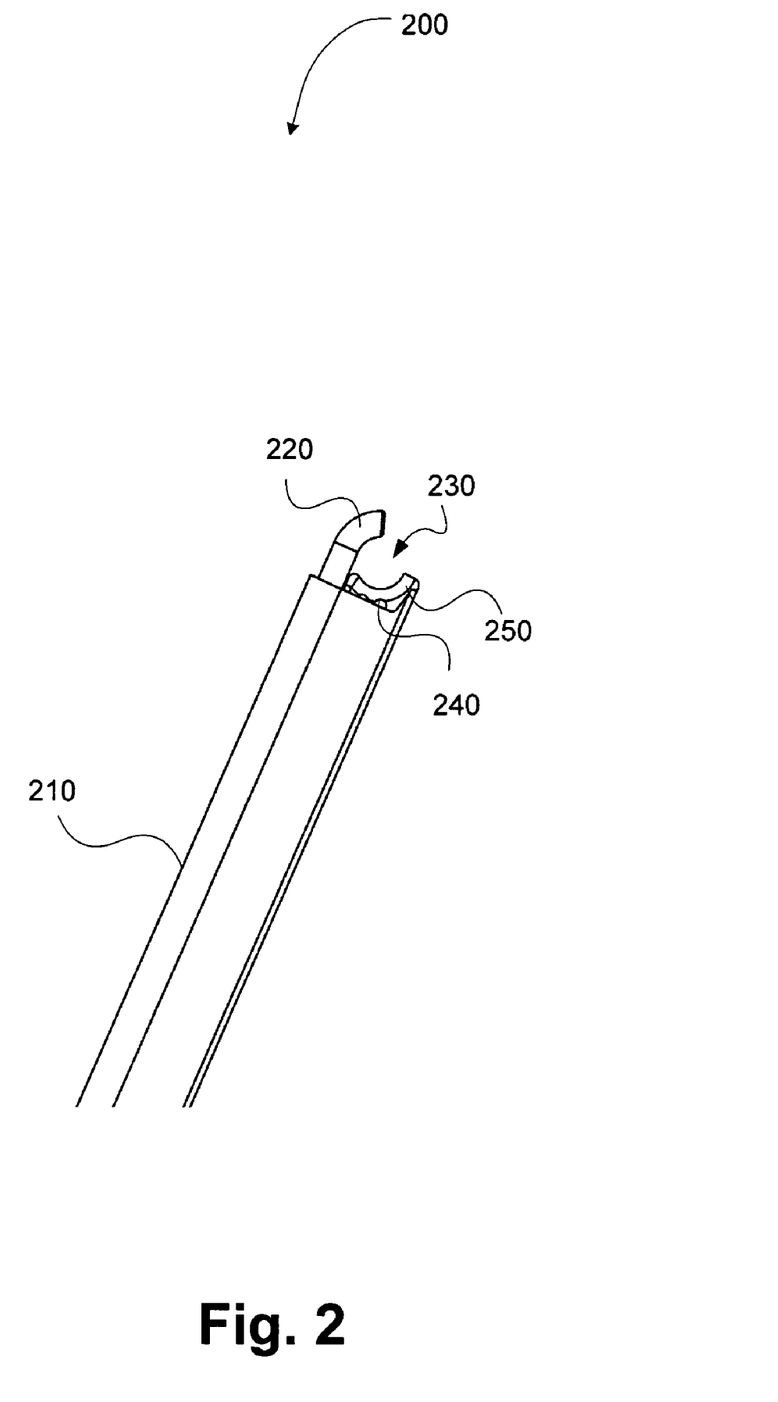
FIG. 2 is a perspective view of a pivoting instrument configured to be used in connection with the pivotable interbody implant of FIGS. 1A and 1B, according to one exemplary embodiment.

FIG. 2 illustrates an exemplary implant manipulation tool (200) that may be used with the present pivotable interbody implant (100). As illustrated in FIG. 2, the present implant manipulation instrument (200) includes an extension member (210) extending from a handle and/or other grasping feature including actuation mechanisms (not shown). At a distal end of the extension member (210) are disposed a number of features configured to facilitate the grasping and subsequent manipulation of the pivotable interbody spacer, according to one exemplary embodiment.

As shown in FIG. 2, the exemplary implant manipulation instrument (200) includes a bottom stationary jaw or protrusion (250) and a top retractable latching mechanism (220). Together, the bottom stationary jaw (250) and the top retractable latching mechanism define a modifiable coupling orifice (230). According to one exemplary embodiment, the coupling orifice may be presented to any number of features of the pivotably interbody implant (100; FIG. 1A), and the coupling orifice may then be manipulated by selectively retracting the retractable latching mechanism (220) to couple a desired feature. According to one exemplary embodiment, the coupling orifice (230) is configured to be used to couple the internal transverse cylinder (116) of the pivotable interbody implant (100; FIG. 1) via the access gap (122). While the present grasping means have been described in the context of actuating a singe retractable latching mechanism, any number of variations on the grasping means can be made including, but in no way limited to the ability to manipulate both upper and lower jaws or latching mechanisms.

Figure 3:
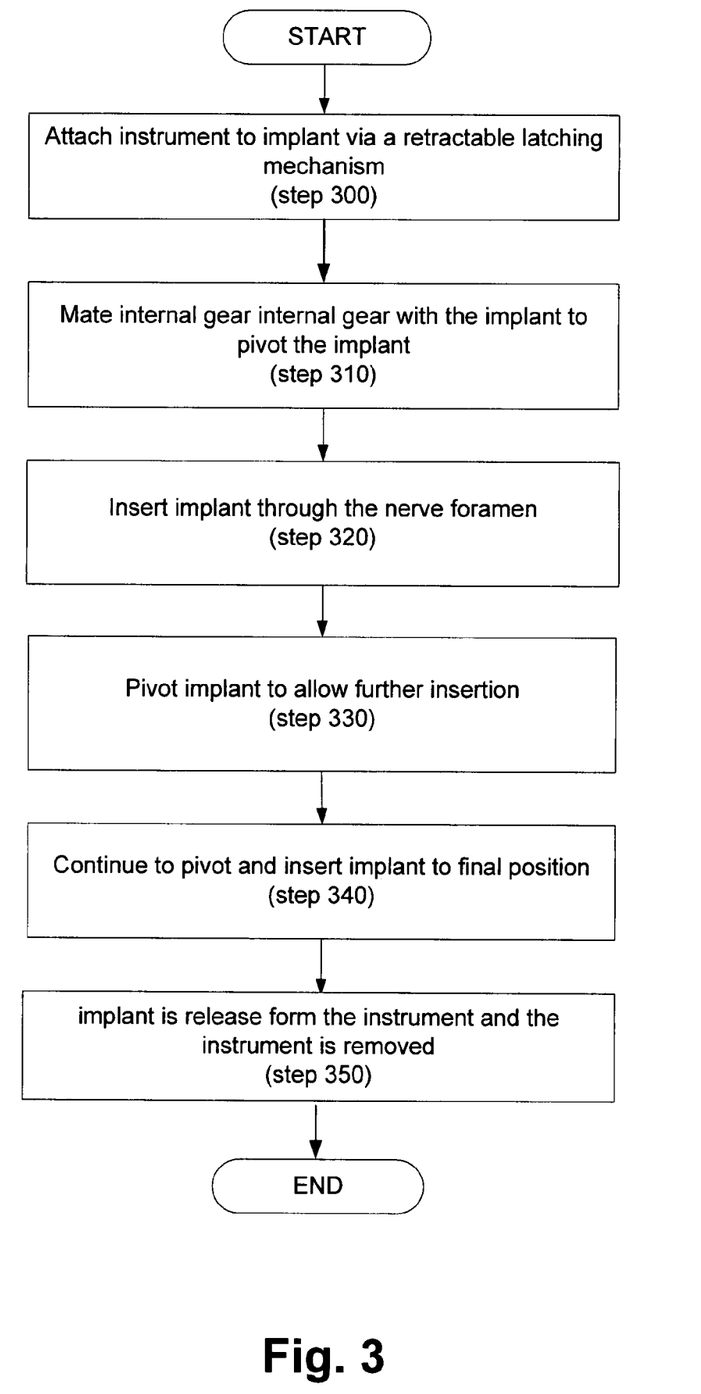
FIG. 3 is a flow chart illustrating a method of pivotably inserting an interbody implant, according to one exemplary embodiment.

Regardless of the grasping mechanism employed by the implant manipulation instrument, the grasping mechanisms are configured to engage the teeth (120) or other frictionally engaging features are formed on the perimeter of at least one end of the implant. As illustrated, the distal end of the exemplary implant manipulation instrument (200) includes a controllable friction transmitter (240). According to one exemplary embodiment, the controllable friction transmitter (240) may be a ratcheting or other internal pivot gear or other toothed mating feature configured to mate with the external teeth (120) of the pivotable interbody implant (100). However, the present exemplary system and method are in no way limited to geared mechanisms. Rather, according to one exemplary embodiment, the controllable friction transmitter may be a wheel or other moveable surface configured to provide friction with the pivotable interbody implant (100) due to a material, a surface finish, or a unique surface feature, protrusion, or recess. Once the controllable friction transmitter (240) is engaged with the external teeth (120) or other frictionally engaging surface or feature, the controllable friction transmitter may be manipulated to pivot and otherwise orient the pivotable interbody implant (100). FIG. 3 illustrates an exemplary method for pivotably manipulating an interbody implant, according to one exemplary embodiment.

Exemplary Method

As illustrated in FIG. 3, the present exemplary method begins by first attaching the implant manipulation instrument to the implant via a retractable latching mechanism or other coupling mechanism present on your implant manipulation instrument (step 300). Once the implant manipulation instrument is attached, the teeth (120) or other frictionally engaging surface on at least one end of the implant is coupled or otherwise mated to the controllable friction transmitter (step 310). Once the pivotable interbody implant is controllably coupled to the implant manipulation instrument (200), the implant can be inserted to a patient for a TLIF implant or other procedure. Again, for ease of explanation, the present disclosure is provided as used for a TLIF implant or other procedure. However, the present system and method may be used for any number of implant applications. Initially, the implant can be inserted though the nerve foramen (step 320). Once the implant can no longer be inserted in its coupling state, the implant may be pivoted to allow for further insertion (step 330). The steps of pivoting and inserting the implant are continued until the implant is in its final position (step 340). Once in a final position, the implant is released from the implant manipulation instrument (200) and the instrument is removed from the patient. Further details of the present exemplary system will be provided below with reference to FIGS. 3-4F.

Figure 4A:
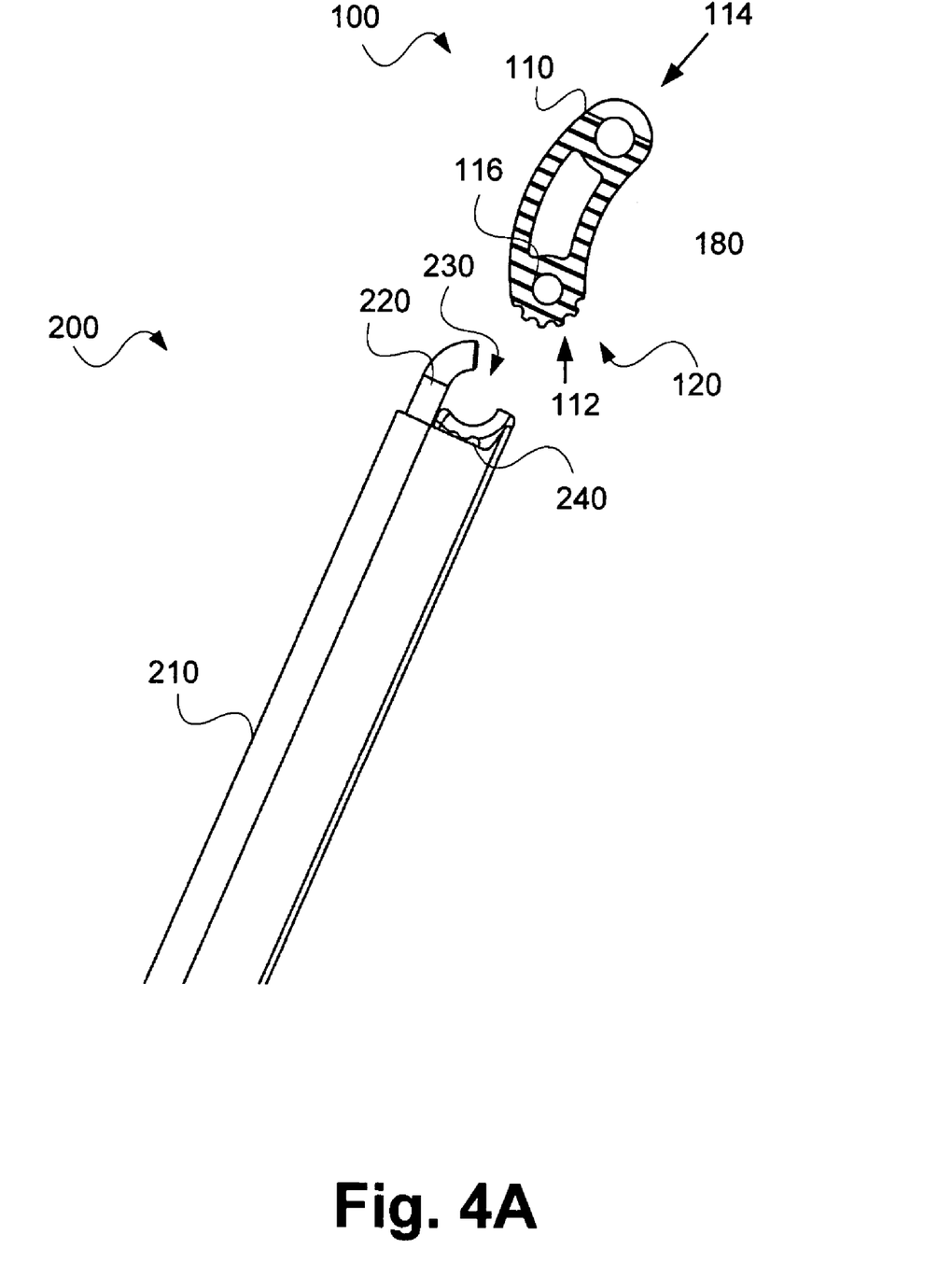
FIGS. 4A-4F are top and perspective views of pivotably inserting an interbody implant using the method of FIG. 3, according to various exemplary embodiments.

As mentioned, the present exemplary system begins by attaching the instrument to the implant via a retractable latching mechanism or other coupling mechanism present on the implant manipulation instrument (step 300). According to one exemplary embodiment, the implant (100) is coupled to the implant manipulation instrument (200) by entering the internal transverse cylinder (116; FIG. 1A) in the coupling orifice (230; FIG. 2) of the implant manipulation instrument (200; FIG. 2). As shown in FIG. 4A, the retractable latching mechanism (220) may be passed through the access gap (122) to draw the pivotable interbody implant (100) into the coupling orifice (230).

Figure 4B:
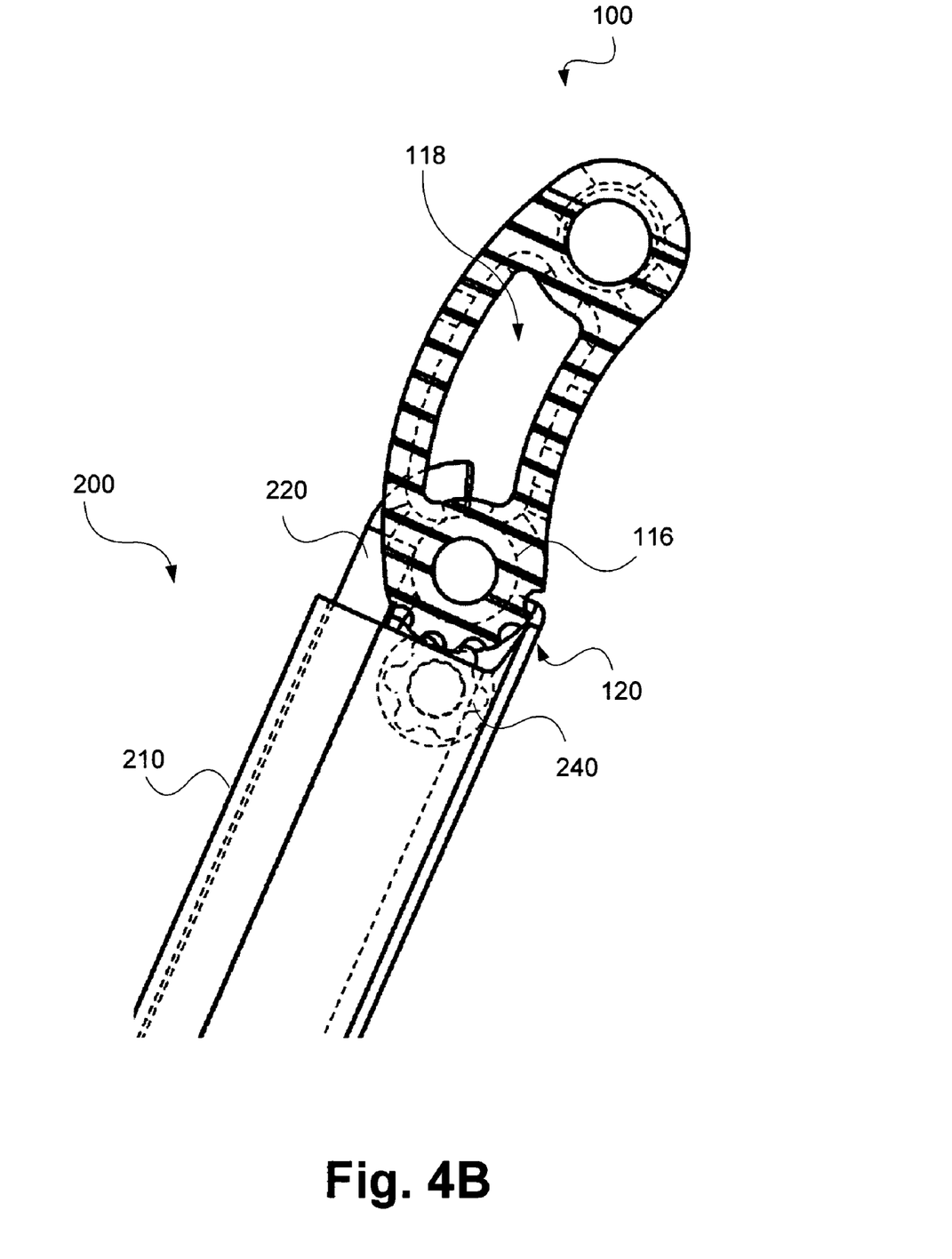

Once the implant manipulation instrument is attached, the teeth (120) or other frictionally engaging surface on at least one end of the implant is coupled or otherwise mated to the controllable friction transmitter (step 310). As illustrated in FIG. 4B, the teeth of a controllable internal gear or other controllable friction transmitter (240) may mesh or otherwise engage the teeth (120) or other frictionally engaging surface on at least one end of the implant such that motion or translation of the controllable friction transmitter (240) causes a pivot of the implant (100) about the internal transverse cylinder (116).

Figure 4C:
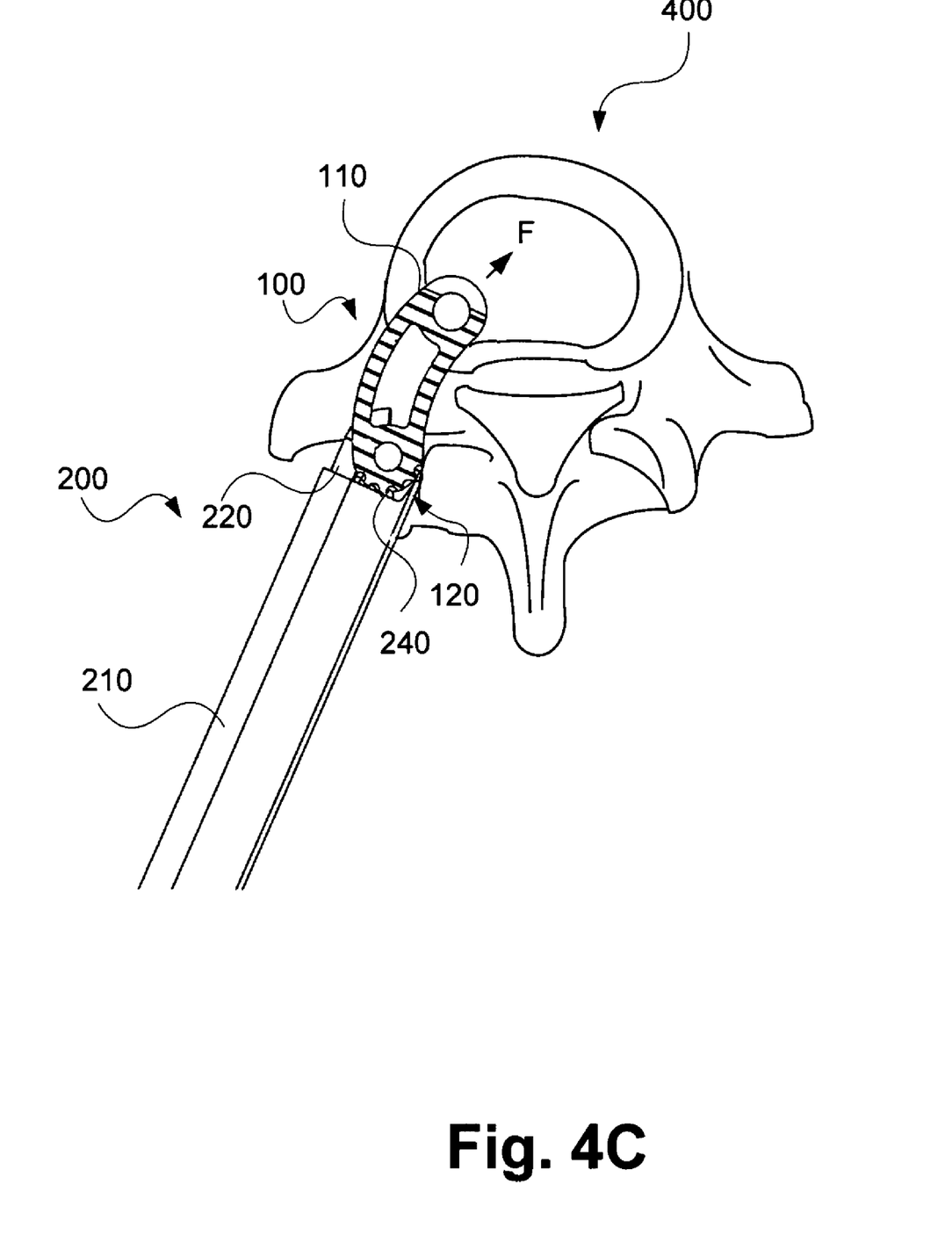

Once the pivotable interbody implant is controllably coupled to the implant manipulation instrument (200), the implant (100) can be inserted to a patient for a TLIF implant procedure or other procedure. As illustrated in FIG. 4C, the procedure can begin similar to traditional procedures by inserting the pivotable interbody implant (100) through the nerve foramen, as indicated by the arrow (F) (step 320), to access space between desired vertebrae (400). This insertion can be substantially identical to traditional insertions if the controllable friction transmitter (240) is kept stationary.

Figure 4D:
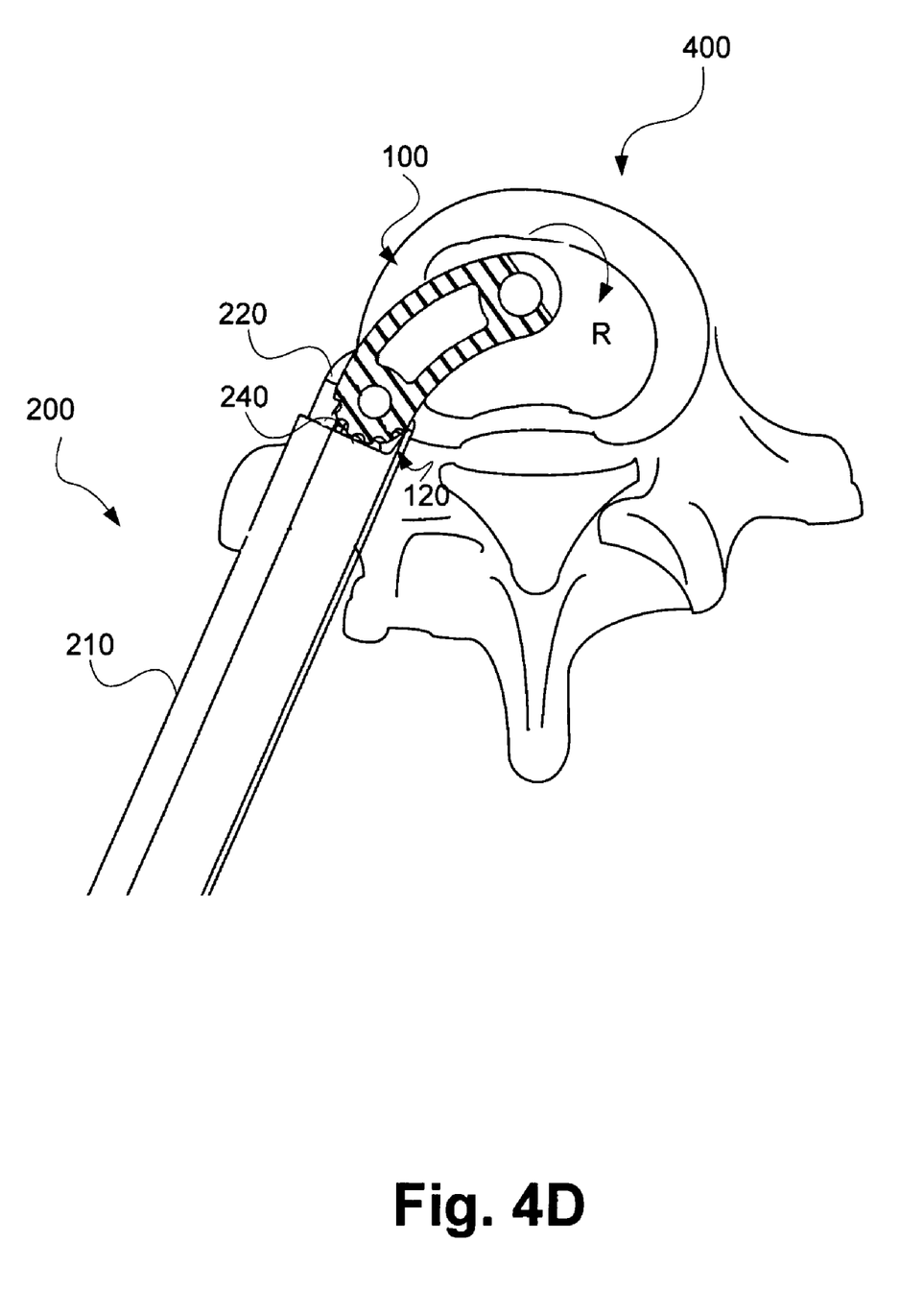

Once the implant can no longer be inserted in its coupled state, the implant may be pivoted to allow for further insertion (step 330). Specifically, as illustrated by the arrow (R) of FIG. 4D, the controllable friction transmitter (240) can be manipulated, such as by an actuation of an internal gear, to cause a rotation of the pivotable interbody implant (100) about an axis. By pivoting the implant (100), obstacles can be avoided and narrow or non-linear passageways can be followed without tamping the implant into place.

Figure 4E:
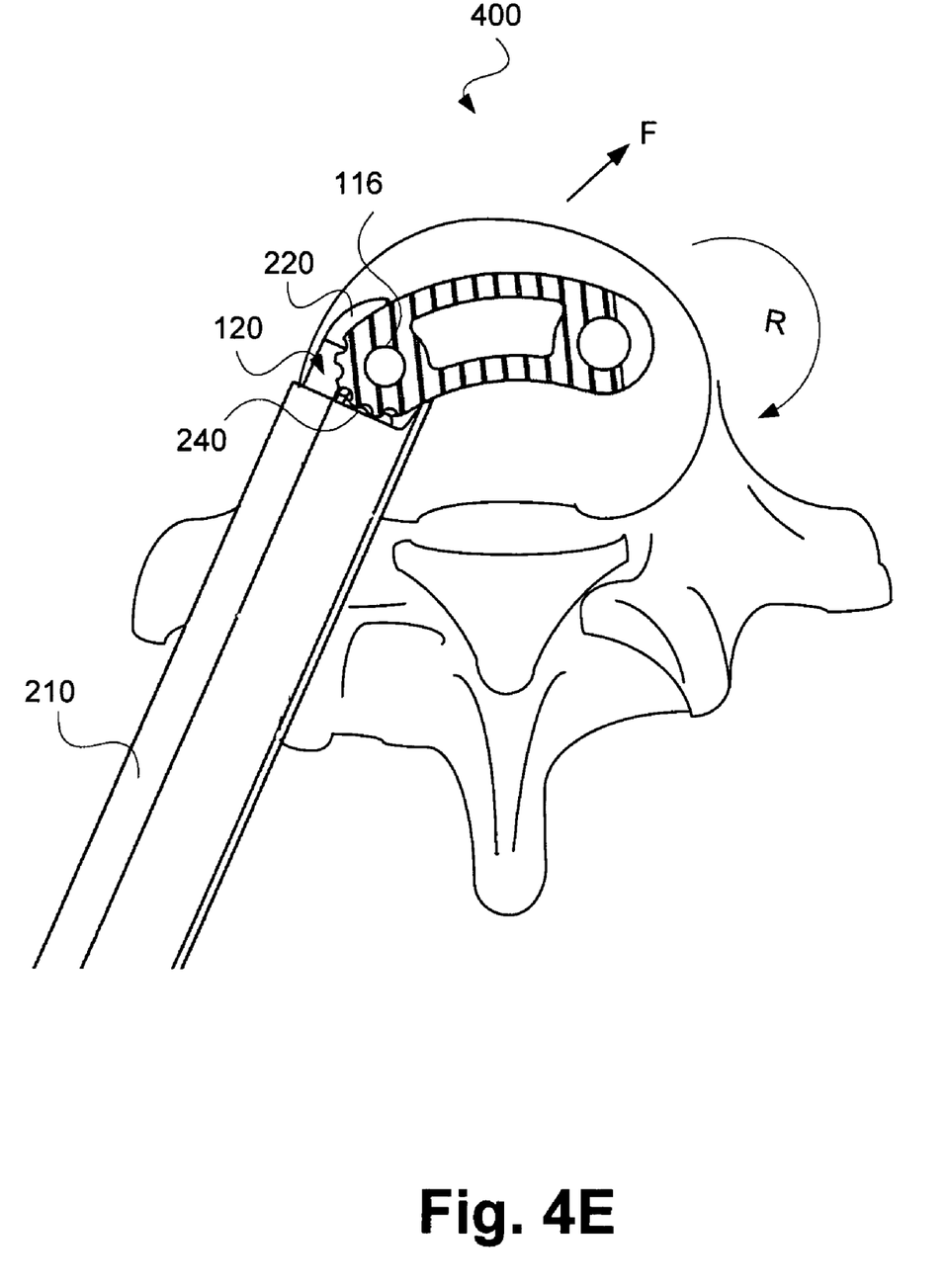
Figure 4F:
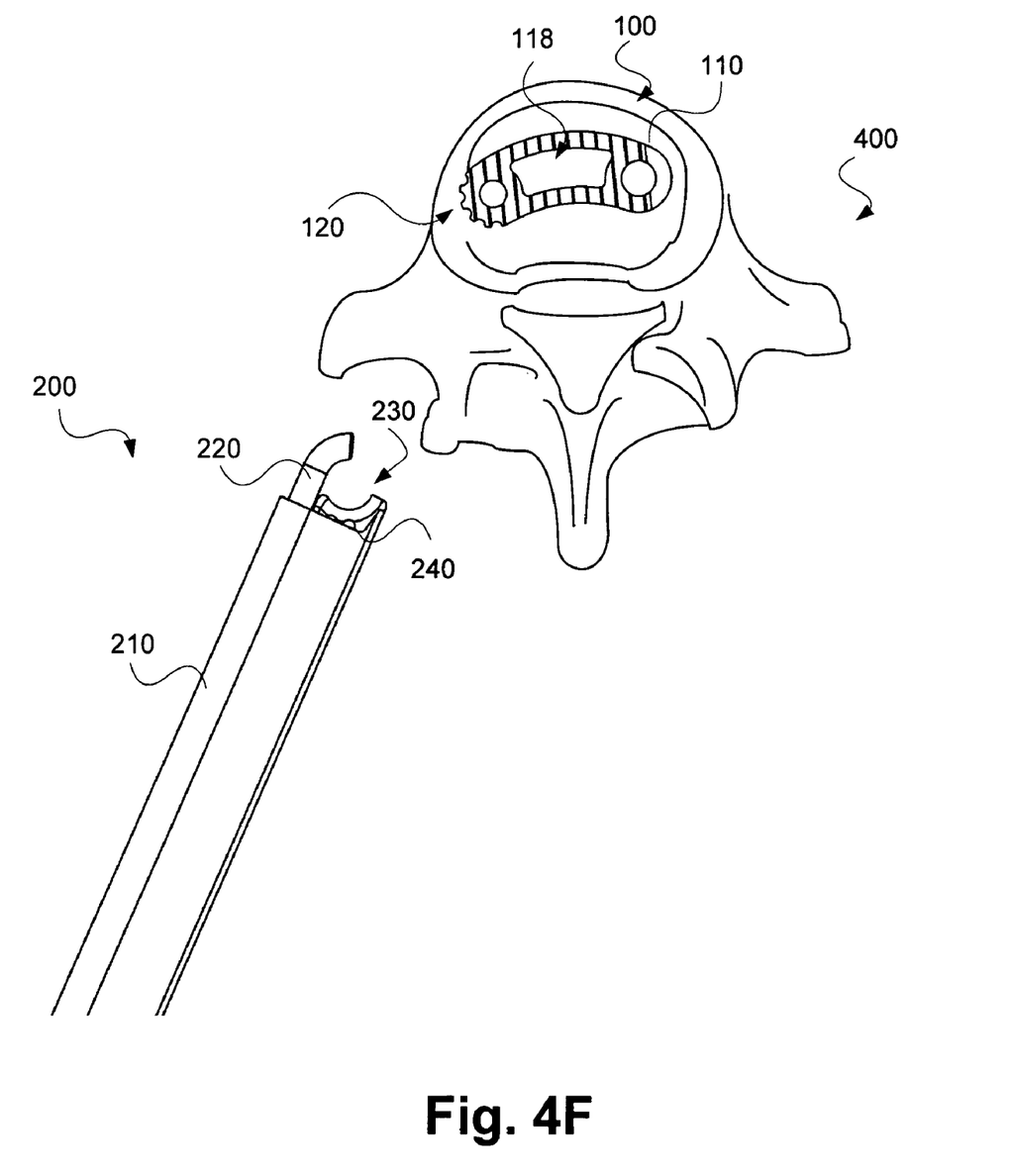

As illustrated in FIG. 4E, the steps of pivoting and inserting the pivotable interbody implant (100) can be continued and repeated until the implant is in its final desired position (step 340). Once in a final position, the pivotable interbody implant (100) is released from the implant manipulation instrument (200) and the instrument is removed from the patient. Particularly, according to the exemplary embodiment illustrated in FIG. 4F, the retractable latching mechanism (220) may be extended to enlarge the coupling orifice (230). Once sufficiently large, the implant releases from the coupling orifice and remains in the desired location as the implant manipulation instrument (200) is retracted and removed from the patient.

In conclusion, the present exemplary systems and methods provide for a pivotable interbody implant that provides a user with the ability to insert the implant in a non-linear path. Additionally, the present exemplary interbody implant (100) employs geometry that provides for a small implant with relatively large surface area and internal cavity. The implant is hollowed out to increase cavity volume and surface area while minimizing overall size. Additionally the present exemplary systems and methods allow for rotation of the implant for final positioning without having to release the implant and tamp the implant into place.

The preceding description has been presented only to illustrate and describe the present methods and systems. It is not intended to be exhaustive or to limit the present system and method to any precise form disclosed. Many modifications and variations are possible in light of the above teaching.

The foregoing embodiments were chosen and described in order to illustrate principles of the system and method as well as some practical applications. The preceding description enables others skilled in the art to utilize the method and system in various embodiments and with various modifications as are suited to the particular use contemplated. It is intended that the scope of the present exemplary system and method be defined by the following claims.

What I claim is:

1. A pivotable interbody implant system, comprising:
    an implant including a body having a distal end and a proximal end, and at least one frictionally engaging feature disposed on at least one of said distal end or said proximal end of said body;
    an insertion instrument configured to selectively pivot said implant including an extension member, an implant coupling mechanism, and a controllable friction transmitter, said controllable friction transmitter operatively engaging said at least one frictionally engaging feature of said implant; and
    means operating said controllable friction transmitter to move said at least one frictionally engaging feature of said implant causing said implant to move relative to said insertion instrument, while said controllable friction transmitter remains engaged with said implant.

2. The pivotable interbody implant system of claim 1, wherein said at least one frictionally engaging feature comprises a plurality of teeth formed on one end of said implant.

3. The pivotable interbody implant system of claim 2, wherein said controllable friction transmitter comprises a gear configured to mesh with said plurality of teeth.

4. The pivotable interbody implant system of claim 1, wherein said at least one frictionally engaging feature comprises one of a surface finish or a material.

5. The pivotable interbody implant system of claim 1, wherein said at least one frictionally engaging feature is disposed on an outer surface of at least one of said distal end or said proximal end of said body.

6. The pivotable interbody implant system of claim 1, wherein said at least one frictionally engaging feature is disposed on an internal surface of at least one of said distal end or said proximal end of said body.

7. The pivotable interbody implant system of claim 1, further comprising an arcuate anterior surface and an arcuate posterior surface.

8. The pivotable interbody implant system of claim 1, wherein said implant coupling mechanism comprises:
   a stationary arcuate protrusion; and
   a retractable arcuate protrusion;
   wherein movement of said retractable arcuate protrusion modifies a coupling space.

9. The pivotable interbody implant system of claim 1, wherein said controllable friction transmitter configured to selectively manipulate said frictionally engaging feature is ratchetable.

10. A method for inserting an interbody implant into a surgical site comprising:
   creating a coupled connection between said interbody implant and an insertion instrument such that said interbody implant is rotatable with respect to said insertion instrument about at least one degree of freedom, said coupled connection including a controllable friction transmitter, said controllable friction transmitter operatively engaging at least one frictionally engaging feature of said implant;
   fixing said interbody implant in a first angular orientation with respect to said insertion instrument;
   inserting said interbody implant into a surgical site;
   operating said controllable friction transmitter on said insertion instrument such that said interbody spacer is moved to a second angular position with respect to said insertion instrument, while said controllable friction transmitter remains in contact with said inter body implant;
   inserting said interbody implant further into said surgical site; and
   releasing said coupled connection between said interplant body implant and said insertion instrument.

11. The method of claim 10 wherein said coupled connection includes a stationary protrusion and a movable protrusion on said insertion instrument;
   operating said movable protrusion and releasing said coupled connection between said insertion instrument and said interbody implant.

12. The method of claim 10 including operating said controllable friction transmitter on said insertion instrument such that said interbody spacer is in a final angular position with respect to said insertion instrument.

* * * * *